US005986015A

United States Patent [19]

Midha et al.

[11] Patent Number: 5,986,015

[45] Date of Patent: Nov. 16, 1999

[54] METHOD OF MAKING GRAFT POLYMERS

[75] Inventors: Sanjeev Midha, Blue Ash; Timothy Roy Nijakowski, Cincinnati, both of Ohio

[73] Assignee: The Procter & Gamble Company, Cincinnati, Ohio

[21] Appl. No.: 08/858,070

[22] Filed: May 16, 1997

[51] Int. Cl.[6] .......... C08C 19/42

[52] U.S. Cl. .......... 525/370; 525/331.4

[58] Field of Search .......... 525/370, 331.4, 525/331.6

[56] References Cited

U.S. PATENT DOCUMENTS

| | | | |
|---|---|---|---|
| 3,928,558 | 12/1975 | Cheesman et al. | 424/47 |
| 4,749,565 | 6/1988 | Grollier | 424/70 |
| 4,933,176 | 6/1990 | van Reeth | 424/70 |
| 4,983,377 | 1/1991 | Murphy et al. | 424/47 |
| 4,988,506 | 1/1991 | Mitra et al. | 424/81 |
| 5,021,477 | 6/1991 | Garbe et al. | 424/70 |
| 5,166,276 | 11/1992 | Hayama et al. | 525/329.7 |
| 5,209,924 | 5/1993 | Garbe et al. | 424/71 |
| 5,565,193 | 10/1996 | Midha et al. | 424/70.12 |
| 5,618,524 | 4/1997 | Bolich, Jr. et al. | 424/70.12 |
| 5,622,694 | 4/1997 | Torgerson et al. | 424/70.122 |
| 5,632,998 | 5/1997 | Midha et al. | 424/401 |
| 5,653,968 | 8/1997 | Carballada et al. | 424/70.11 |
| 5,653,969 | 8/1997 | Carballada et al. | 424/70.16 |
| 5,658,557 | 8/1997 | Bolich, Jr. et al. | 424/70.12 |
| 5,662,892 | 9/1997 | Bolich, Jr. et al. | 424/70.1 |
| 5,665,337 | 9/1997 | Carballada et al. | 424/70.12 |
| 5,667,771 | 9/1997 | Carballada et al. | 424/70.12 |
| 5,730,966 | 3/1998 | Torgerson et al. | 424/70.11 |
| 5,753,216 | 5/1998 | Leitch et al. | 424/70.12 |

FOREIGN PATENT DOCUMENTS

| | | | |
|---|---|---|---|
| WO 9718247 | 11/1995 | WIPO . | |
| WO 96/30421 | 10/1996 | WIPO | C08F 297/00 |

OTHER PUBLICATIONS

U.S. application No. 08/800,935, filed Feb. 13, 1997, Dubois et al.

U.S. application No. 08/799,903, filed Feb. 13, 1997, Dubois et al.

U.S. application No. 08/858,071, filed May 16, 1997, Midha et al.

U.S. application No. 08/842,954, filed Apr. 25, 1997, Midha et al.

U.S. application No. 08/846,058 filed Apr. 25, 1997, Midha et al.

U.S. application No. 08/854,513, filed May 12, 1997, Midha et al.

U.S. application No. 08/854,698, filed May 12, 1997, Midha et al.

Patten, *Polymer Preprints,* Amer. Chem. Soc., 37(1), pp. 575–576, 1996.

Nakagawa et al. *Polymer Preprints,* 37(1), pp. 577–578, 1996.

*Primary Examiner*—Robert Dawson
*Assistant Examiner*—D. Aylward
*Attorney, Agent, or Firm*—William J. Winter; Tara M. Rosnell

[57] ABSTRACT

Disclosed is an improved method of making hydrophobic and hydrophilic graft polymers, which method comprises the steps of (a) reacting copolymerizable monomers to form an organic polymeric backbone having a weight average molecular weight of from about 15,000 grams/mole to about 200,000 grams/mole and a plurality of organic halide moieties covalently bonded to the polymeric backbone and pendant from the polymeric backbone and then, without a separate purification or isolation step; (b) reacting copolymerizable monomers with the organic halide moieties of the polymeric backbone by atom transfer free radical polymerization in the presence of a catalytic amount of a Cu(I) salt or other transition metal species complexed to a ligand suitable for solubilizing the salt in the reaction mixture to form a plurality of polymeric side chains covalently bonded to the polymeric backbone and pendant from the polymeric backbone and having a weight average molecular weight of from about 500 grams/mole to about 200,000 grams/mole, wherein the polymeric back bone and the plurality of polymeric side chains form hydrophilic and hydrophobic graft polymers having a weight average molecular weight of from about 16,000 grams/mole to about 10,000,000 grams/mole.

26 Claims, No Drawings

METHOD OF MAKING GRAFT POLYMERS

TECHNICAL FIELD

The present invention relates to an improved method of making hydrophobic and hydrophilic graft polymers suitable for use in personal care compositions.

BACKGROUND OF THE INVENTION

Personal care compositions such as hair sprays, styling shampoos, cosmetics, skin care products, and the like, often contain film-forming polymers for various reasons. These film-forming polymers are especially useful in hair care compositions to provide hair styling performance to the composition. Film-forming polymers for use in such compositions include organic or silicone-containing, linear or graft, copolymers which contain various monomers in an alternating, random, block or homopolymer configuration.

Graft copolymers are well known for use as film-forming polymers in hair care and other personal care compositions. These graft copolymers typically comprise a polymeric backbone and one or more macromonomers grafted to the backbone, wherein the physical and chemical attributes such as glass transition temperature values (Tg), water solubility, and so forth are selected for the polymeric backbone and macromonomer grafts so as to provide the desired film-forming properties and other chemical or physical properties of the copolymers in a personal care composition. The graft copolymers are especially versatile in that the polymeric backbone and the attached macromonomer grafts can have select or different chemical or physical properties which collectively provide the optimal formulation or performance profile for the intended personal care composition in which it will be used.

Synthesis of graft copolymers, however, is typically more difficult than synthesis of many copolymers, especially linear polymers. Unlike linear polymer synthesis, the synthesis of graft copolymers typically involves a separate polymerization step involving the making of a macromonomer containing a reactive end group, copolymerization of the macromonomer with a copolymerizable, ethylenically unsaturated monomer, and then termination of this last copolymerization step to obtain the desired graft polymers.

It has now been found that hydrophobic and hydrophilic graft polymers can now be made by simpler, more effective synthesis methods, and that these new synthesis methods result in the formation graft polymers which when applied to the hair or other surface form a polymeric film or weld having improved adhesive and cohesive strength. These polymers are very useful when used as film-forming polymers in personal care compositions, especially when used as film-forming or styling polymers in hair styling compositions. The graft polymers in these hair styling compositions provide improved styling and/or conditioning performance, and are especially effective in providing improved durability of hair style and improved hair feel.

It is therefore an object of the present invention to provide an improved method for making graft polymers, and further to provide such a method for making graft polymers for use in personal care compositions, and yet further to provide such a method which involves fewer synthesis steps than other conventional methods of making graft polymers.

SUMMARY OF THE INVENTION

The present invention is directed to an improved method of making graft polymers, which method comprises the steps of (a) reacting copolymerizable monomers to form an organic polymeric backbone having a weight average molecular weight of from about 15,000 grams/mole to about 9,800,000 grams/mole and a plurality of organic halide moieties covalently bonded to the polymeric backbone and pendant from the polymeric backbone and then, without a separate purification or isolation step; (b) reacting copolymerizable monomers with the organic halide moieties of the polymeric backbone by atom transfer free radical polymerization in the presence of a catalytic amount of a transition metal species, preferably a Cu(I) salt complexed to a ligand suitable for solubilizing the salt in the reaction mixture, to form a plurality of polymeric side chains covalently bonded to the polymeric backbone and pendant from the polymeric backbone and having a weight average molecular weight of from about 500 grams/mole to about 200,000 grams/mole, wherein the polymeric back bone and the plurality of polymeric side chains form graft polymers having a weight average molecular weight of from about 16,000 grams/mole to about 10,000,000 grams/mole.

It has been found that the new process allows for a simpler, more effective, synthesis of graft polymers using fewer process steps than conventional synthesis methods, and also allows for the synthesis of graft polymers without reliance upon the use of copolymerizable macromonomers, or a separate synthesis step for making such macromonomers. It has also been found that personal care compositions containing these graft polymers contain low or reduced concentrations of polymer contaminants such as ungrafted polymeric backbone and/or unattached polymeric grafts or side chains, wherein the graft polymers also have a low or reduced polydispersity.

DETAILED DESCRIPTION OF THE INVENTION

The method of the present invention comprises two key reactions steps. In a first reaction step, copolymerizable monomers are reacted together to form a polymeric backbone containing organic halide moieties covalently bonded to and pendant from the backbone. In a second subsequent reaction step, the polymeric backbone is reacted with copolymerizable monomers by atom transfer radical polymerization in the presence of a catalytic amount of a Cu(I) salt or other transition metal species, preferably complexed to a suitable ligand. Each of these two essential process steps are described in detail hereinafter.

The terms "hydrophilic" or "water soluble" as used herein, unless otherwise specified, are used interchangeably and refer to polymers (or salt forms of such polymers produced by neutralization or quaternization of acidic or basic groups) or other materials that are soluble in distilled water, ethanol, n-propanol, isopropanol, or combinations thereof, at 25° C. and at a concentration of 0.2% by weight of such polymer or other material. The terms "hydrophobic" and "water insoluble" as used herein, unless otherwise specified, are used interchangeably and refer to all other polymers or materials that are not hydrophilic as defined herein.

The method of the present invention can comprise, consist of, or consist essentially of the essential elements or limitations of the invention described herein, as well as any of the additional or optional elements or limitations described herein.

All molecular weights as used herein, unless otherwise specified, are weight average molecular weights expressed as grams/mole.

All percentages, parts and ratios are by weight of the total referenced composition, unless otherwise specified. All such weights as they pertain to listed ingredients are based on the active level and, therefore, do not include solvents or by-products that may be included in commercially available materials, unless otherwise specified.

Synthesis Method

The method of the present invention is directed to an improved synthesis of graft polymers, which method comprises two essential reaction steps. In the first reaction step, the polymeric backbone of the graft polymers herein are first prepared. This is accomplished by reacting copolymerizable monomers to form a polymeric backbone containing a plurality of organic halide moieties covalently bonded to and pendant from the polymeric backbone, and includes those polymers which conform generally to the formula

where "A" is a monomer unit having an organic halide moiety "C" attached which is covalently bonded to and pendant from the "A" monomer unit, and "B" is a monomer unit that is copolymerizable with the "A" monomer unit, "a" is a positive integer having a value of 2 or greater, preferably a value of from about 2 to about 30, and "b" is a positive integer having a value of at least about 4, preferably a value of from about 10 to about 2000. The organic halide moiety "C" includes any linear, branched or cyclic (aromatic or otherwise) carbon structure, whether substituted or unsubstituted, which also contain a halogen atom (Fl, Cl, Br or I).

In the first reaction step of the synthesis method herein, the "A" monomer unit with the attached organic halide moiety "C" is preferably selected from the group of allyl monomers, vinyl acetate monomers, acid halide monomers, styryl monomers, or combination thereof, and more preferably selected from the monomer units characterized by the following general structures (Groups I–V):

(I)

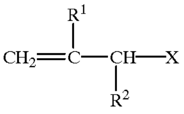

(II)

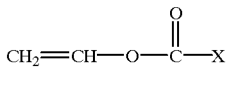

(III)

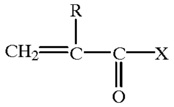

(IV)

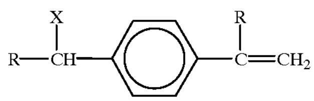

(V)

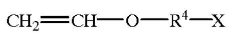

where R is methyl or hydrogen; X is a halogen atom (Fl, Cl, Br, I); $R^1$ and $R^2$ are each independently selected from methyl, hydrogen or methoxy; and $R^4$ is an alkyl group having from 1 to 8 carbon atoms.

The first reaction step of the process herein involves any conventional or otherwise known polymerization techniques such as ionic, Ziegler-Natta, free radical, group transfer or step growth polymerization, or combinations thereof. The first reaction step preferably involves conventional free radical polymerization techniques. Once the first reaction is complete, or has progressed to the extent desired, the first reaction step is terminated or allowed to terminate depending on the polymerization method selected, the degree or extent of polymerization desired, the reactivity of the monomer units selected for use in the reaction, and so forth. Any conventional or otherwise known termination technique appropriate for the selected reaction and reaction conditions may be used. For example, and most typically, after polymerization of the polymeric backbone by free radical polymerization, the reaction mixture is heated to about 120° C. for about 15 minutes to consume or react any remaining free radical initiator, and thereafter the reaction mixture is cooled or allowed to cool to room temperature to allow the reaction to self terminate before addition of ingredients to start the second reaction step.

In the second reaction step of the process of the present invention, the polymeric backbone described hereinabove is reacted with one or more copolymerizable monomers in the presence of a catalytic amount of a transition metal salt, preferably a Cu(I) salt and preferably complexed to a suitable ligand. In this reaction step, the organic halide moieties act as initiators in the presence of the copolymerizable monomers and the catalyst, resulting in the grafting of the monomers onto the polymeric backbone by atom transfer free radical polymerization, the monomers forming a plurality of polymeric side chains covalently bonded to and pendant from the backbone. The polymeric side chains form on the polymeric backbone without the need to use copolymerizable macromonomers to achieve the pendant polymeric graft chains.

The catalyst for the second reaction step is a transition metal salt, preferably a Cu(I) salt such as Cu(I) halide salts (Cl, Fl, Br, I) and which is preferably complexed to a ligand which is suitable for solubilizing the Cu(I) salt in the reaction mixture, wherein the reaction mixture of the second reaction step comprises dissolved or partially dissolved polymer, unreacted monomer, solvent and catalyst. Preferred ligands for use in solubilizing the Cu(I) salts in the reaction mixture are aprotic bidendates such as diphosphates, 2,2'bipyridyl, C1–C20 alkyl substituted bipyridyl (4,4'-di-5-nonyl-2,2'-bipyridine, 4,4'-di-tert-butylbipyridine, 4,4'-diheptyl-2,2'-bipyridine) and combinations thereof. Most preferred is 2,2'bipyridyl complexed to a Cu(I) halide salt, especially Cu(I) Cl. Other conventional or otherwise known ligands can be used herein provided that they do not substantially and unduly impair the polymerization reaction of the process herein, some examples of which are described in "The Use of Living Radical Polymerization to Synthesize Graft Copolymers" Dept. of Chemistry, Carnegie Mellon University, Pittsburgh, Pa.; Kathryn L. Beers, et al., Polymer Preprints, Vol. 37(1), pg. 571–572, 1996. "Alternating Copolymers of Methyl Acrylate with Isobutene and Isobutyl Vinyl Ether using ATRP" Dept. of Chemistry, Carnegie Mellon University, Pittsburgh, Pa.; Simion Cocoa and Krzysztof Matyjaszewski Polymer Preprints, Vol. 37(1), pg. 573–574, 1996., "Radical Polymerization yielding Polymers with Mw/Mn ~1.05 by Homogeneous Atom Transfer Radical Polymerization" Carnegie Mellon University, Pittsburgh, Pa.; T. E. Patten et al. Polymer Preprints, Vol. 37(1), pg. 575–576, 1996. "The Synthesis of End Functional Polymers by Living Radical Polymerization" Carnegie Mellon University, Pittsburgh, Pa., Y. Nakagawa et al., Polymer Preprints, Vol. 37(1), pg. 577–578, 1996, which publications are incorporated herein by reference.

Graft Polymers

The synthesis method of the present invention is especially useful for making hydrophobic or hydrophilic, film-forming polymers suitable for use in personal care compositions such as hair styling compositions. Graft polymers made in accordance with this method typically have a low or reduced polydispersity and contain reduced concentrations of polymer contaminants such as ungrafted polymeric backbone and/or unattached polymeric grafts or side chains once the two step reaction steps of the synthesis are complete.

Graft polymers made in accordance with the synthesis method herein are characterized by a hydrophilic or hydrophobic polymeric backbone with a plurality of hydrophobic or hydrophilic polymeric side chains covalently bonded to and pendant from the polymeric backbone, wherein the polymeric backbone represents from about 50% to about 99%, preferably from about 60% to about 98%, more preferably from about 75% to about 95%, by weight of the graft polymer, and the plurality of polymeric side chains represent from about 1% to about 50%, preferably from about 2% to about 40%, more preferably from about 5% to about 25%, by weight of the graft polymer.

The polymeric side chains on the graft polymers have a weight average molecular weight of at least about 500 grams/mole, preferably from about 1,000 grams/mole to about 200,000 grams/mole, more preferably from about 1,500 grams/mole to about 30,000 grams/mole, most preferably from about 3,000 grams/mole to about 25,000 grams/mole. These polymeric side chains may comprise monomer units arranged in an alternating, random, block or homopolymer configuration, and each of the polymeric side chains may comprise the same or different monomers, arranged in the same or different configuration.

The graft polymers made in accordance with the methods herein have a weight average molecular weight of from about 16,000 grams/mole to about 10,000,000 grams/mole, preferably less than about 5,000,000 grams/mole, more preferably less than about 3,000,000. Most preferred are weight average molecular weights of from about 50,000 grams/mole to about 2,000,000 grams/mole, more preferably from about 75,000 grams/mole to about 1,000,000 grams/mole, and even more preferably from about 75,000 grams/mole to about 750,000 grams/mole.

The graft polymers made in accordance with the methods herein can have a single Tg value and preferably are copolymers having at least two distinct immiscible phases, wherein the polymeric side chains are closely associated with each other and exist in one phase and the polymeric backbone of the copolymer remains in a second separate phase. A consequence of this phase immiscibility is that if the temperature separation between each of the Tg values involved is large enough then these copolymers exhibit two distinct glass transition temperatures, namely one Tg value for the backbone and one Tg value for the side chain. The copolymers can also exhibit a third glass transition temperature corresponding to any optional polysiloxane side chains on the graft copolymers. Whether such a third Tg value is observable depends upon a number of factors including the percent silicone in the copolymer, the number of polysiloxane side chains in the copolymer, the temperature separation between each of the Tg values involved, and other such physical factors.

The graft polymers made in accordance with the methods herein also preferably have a polydispersity of less than about 10, preferably less than about 5, even more preferably less than about 4.

Monomers suitable for use in the synthetic methods herein can be hydrophilic or hydrophobic. In this context, the term "hydrophobic monomers" are those copolymerizable monomers which when reacted together form hydrophobic or water insoluble homopolymers, and the term "hydrophilic monomers" refers to those copolymerizable monomers which when reacted together form hydrophilic or water soluble homopolymers.

Monomers suitable for use herein must be copolymerizable and have the requisite characteristics defined herein for use in the synthetic method. These copolymerizable monomers are preferably ethylenically unsaturated monomers, more preferably copolymerizable vinyl monomers. The term "copolymerizable" as used herein means that a material can be reacted with another material in accordance with the first and/or second polymerization reaction steps of the synthesis method herein, whichever is appropriate. The term "ethylenically unsaturated" as used herein refers to monomers that contain at least one polymerizable carbon-carbon double bond (which can be mono-, di-, tri-, or tetra-substituted).

Such copolymerizable monomers include the copolymerizable organic halide-containing monomers described hereinbefore, and also includes the monomer units that arc reacted with the organic halide-containing monomers in the first reaction step of the synthesis method, and also includes the monomer units that are reacted with the polymeric backbone in the second reaction step of the synthesis method.

Copolymerizable monomers for use in the first and second reaction steps of the synthesis method may be the same, or may include combinations of two of more different but copolymerizable monomers, including combinations of hydrophilic and hydrophobic monomers, combinations of copolymerizable monomers having different but select glass transition temperatures (Tg), combinations of polar and nonpolar monomers, and so forth, or combinations of two or more copolymerizable monomers from a single chemical class or otherwise having similar physical or chemical characteristics. The graft polymers may therefore comprise the same or different monomer units, and may therefore be classified as homopolymers, copolymers, terpolymers and so forth.

Nonlimiting classes of monomers useful herein include monomers selected from the group consisting of unsaturated alcohols, unsaturated monocarboxylic acids, unsaturated dicarboxylic acids, unsaturated anhydrides, alcohol esters of unsaturated monocarboxylic acids, alcohol esters of unsaturated dicarboxylic acids, alcohol esters of unsaturated anhydrides, alkoxylated esters of unsaturated monocarboxylic acids, alkoxylated esters of unsaturated dicarboxylic acids, alkoxylated esters of unsaturated anhydrides, aminoalkyl esters of unsaturated monocarboxylic acids, aminoalkyl esters of unsaturated dicarboxylic acids, aminoalkyl esters of unsaturated anhydrides, amides of unsaturated monocarboxylic acids, amides of unsaturated dicarboxylic acids, amides of unsaturated anhydrides, salts of unsaturated monocarboxylic acids, salts of unsaturated dicarboxylic acids, salts of unsaturated anhydrides, unsaturated hydrocarbons, unsaturated heterocycles, and mixtures thereof.

Representative examples of such monomers include acrylic acid (produced by hydrolysis of trimethylsilyl acrylate), methacrylic acid (produced by hydrolysis of trimethylsilyl methacrylate) trimethylsilyl acrylate, trimethylsilyl methacrylate, acrylamide, acrylate alcohols produced by hydrolysis of trimethylsilyl protected alcohol, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (such as that produced by the hydrolysis of vinyl acetate after polymerization), vinyl caprolactam, methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol(2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-tri methyl-1-hexanol, 1-decanol, 1-dodecanol, 1-hexadecanol, 1-octa decanol, and the like, the alcohols having from about 1–18 carbon atoms with the number of carbon atoms preferably being from about 1–12; dicyclopentenyl acrylate; 4-biphenyl acrylate; pentachlorophenyl acrylatc; 3,5-dimethyladamantyl acrylate; 3,5-dimethyladamentyl methacrylate; 4-methoxycarbonylphenyl methacrylate; trimethylsilyl acrylate, trimethylsilyl methacrylate; styrene; alkyl substituted styrenes including alpha-methylstyrene and t-butylstyrene; vinyl esters, including vinyl acetate, vinyl neononanoate, vinyl pivalate and vinyl propionate; vinyl chloride; vinylidene chloride; vinyl toluene; alkyl vinyl ethers, including isobutyl vinyl ether and s-butyl vinyl ether; butadiene; cyclohexadiene; bicycloheptadiene; 2,3-dicarboxylmethyl-1,6-hexadiene; ethylene; propylene; indene; norbomnylene; β-pinene, α-pinene; salts of acids and amines listed above, and combinations thereof. The quaternized monomers can be quaternized either before or after the copolymerization with other monomers of the graft copolymer.

Preferred monomers include acrylic acid (produced by hydrolysis of trimethylsilyl acrylate), methacrylic acid (produced by hydrolysis of trimethylsilyl methacrylate), vinyl pyrrolidone, acrylic or methacrylic acid esters of $C_1$–$C_{18}$ alcohols, trimethylsilyl acrylate, trimethylsilyl methacrylate, styrene, alpha-methylstyrene, t-butylstyrene, vinyl acetate, vinyl propionate, 2-methoxyethyl acrylate, 2-ethoxyethyl acrylate, n-butyl methacrylate, isobutyl methacrylate, t-butyl acrylate, t-butyl methacrylate, 2-ethylhexyl methacrylate, methyl methacrylate, and mixtures thereof.

The suitable copolymerizable monomers described herein are meant to include those corresponding copolymerizable monomers that are unsubstituted or substituted with one or more substituent groups, provided that such groups do not unduly impair the polymerization reactions of the synthesis method. Examples of suitable substituent groups include, but are not limited to, alkyl, aryl, carboxyl, halo groups, and combinations thereof.

Specific examples of hydrophilic graft polymers made in accordance with the methods of the present invention include, but are not limited to, Poly(2-methoxyethyl acrylate-co-methacrylic acid-co-tert-butyl acrylate-co-4-chloromethyl styrene)-graft-poly(styrene-co-methacrylic acid) molecular weight of 150,000 grams/mole, Composition: 2-methoxyethyl acrylate (31.6%), methacrylic acid (22%), tert-butyl acrylate (28%) 4-chloromethyl styrene (0.4%), styrene (18%)

Poly(2-methoxyethyl acrylate-co-methacrylic acid-co-tert-butyl acrylate-co-4-chloromethyl styrene)-graft-[poly styrene-co-methacrylic acid);poly (dimethylsiloxane)]; molecular weight of 150,000 grams/mole, Composition: 2-methoxyethyl acrylate (26.6%), methacrylic acid (22%), tert-butyl acrylate (28%) 4-chloromethyl styrene (0.4%), poly (dimethsiloxane) macromonomer (molecular weight 10,000 grams/mole) (5%) styrene (18%).

Poly(t-butyl acryate-co-2-methoxyethyl acrylate-co-acrylic acid-co-4-chloromethyl styrene)-graft-poly(isobutyl methacrylate-co-methacrylic acid); molecular weight 80,000 grams/mote; Composition: t-butyl acrylate (22%), 2-methoxyethyl acrylate (31%), acrylic acid (18%), 4-chloromethyl styrene (1%), isobutyl methacrylate (15%), methacrylic acid (13%)

Poly(vinyl acetate-co-vinyl pyrollidone-co-chlorovinyl acetate)-graft-poly(styrene-co-methacrylic acid); molecular weight 120,000 grams/mole; Composition: vinyl acetate (40%), vinyl pyrollidone (39%), chlorovinyl acetate (1%), isobutyl methacrylate (10%), dimethylaminoethyl methacrylate (10%).

The hydrophilic graft polymers made in accordance with the synthesis methods herein may comprise acidic functionalities, such as carboxyl groups, and are usually used in at least partially neutralized form to promote solubility or dispersability of the polymer. In addition, use of the neutralized form aids in the ability of the hair styling compositions to be removed from the hair by shampooing. The extent of such neutralization ranges from about 10% to 100%, more preferably from about 20% to about 90%, even more preferably from about 40% to about 85%, neutralization of the acidic functionalities of the graft polymer.

Neutralization of the hydrophilic graft polymers containing acidic functionalities may be accomplished by any conventional or otherwise known technique for affecting such neutralization by using an organic or inorganic base material. Metallic bases are particularly useful for this purpose. Suitable base neutralizers include, but are not limited to, ammonium hydroxides, alkali metal hydroxides, or an alkaline earth metal hydroxides, preferably potassium hydroxide and sodium hydroxide. Examples of other suitable neutralizing agents include, but are not limited to, amines or amino alcohols such as 2-amino-2-methyl-1,3-propanediol (AMPD), 2-amino-2-ethyl-1,3-propanediol (AEPD), 2-amino-2-methyl-1-propanol (AMP), 2-amino-1-butanol (AB), monoethanolamine (MEA), diethanolamine (DEA), triethanolamine (TEA), monoisopropanolamine (MIPA), diisopropanolamine (DIPA), triisopropanolamine (TIPA) and dimethyl stearamine (DMS) and combinations thereof. Preferred are amines and metallic bases.

Neutralization of hydrophilic polymers containing basic functionalities, e.g., amino groups, are likewise preferably at least partially neutralized with an organic or inorganic acid e.g., hydrogen chloride. Neutralization can be accomplished by any conventional or otherwise known technique for accomplishing such neutralization. The preferred extent of neutralization is the same as that described for neutralization of acidic functionalities. Solubility for any neutralized graft polymer made in accordance with the synthesis method herein should be determined only after the desired acid or base neutralization.

Specific examples of hydrophobic graft polymers made in accordance with the methods of the present invention include, but are not limited to, Poly(tert-butyl acrylate-co-2-ethylhexyl methacrylate-co-chloromethyl styrene)-graft-poly(n-butyl acrylate); molecular weight 100,000 grams/mole; Composition; tert-butyl acrylate(54%), 2-ethylhexyl methacrylate (10%), 4-chloromethyl styrene (6%); n-butyl acrylate (30%)

Poly(t-butyl acrylate-co-2-methoxyethyl acrylate-co-4-chloromethyl styrene)-graft-poly(styrene); molecular weight 100,000 grams/mole; Composition: t-butyl acrylate (25%), 2-methoxyethyl acrylate (50%), 4-chloromethyl styrene (2%); styrene(23%)

Poly(vinyl acetate-co-vinyl pyrollidone-co-chlorovinyl acetate)-graft-poly(2-ethylhexyl acrylate); molecular weight 120,000 grams/mole; Composition: vinyl acetate (40%), vinyl pyrollidone (10%), chlorovinyl acetate (5%), 2-ethylhexyl acrylate.(45%)

Optional Silicone Grafts

The synthesis method of the present invention may further comprise the copolymerization of silicone macromonomers with other copolymerizable monomers described herein during the first reaction step of the synthesis method of the present invention, to thus form a polymeric backbone comprising one or more silicone-grafted side chains and a plurality of organic halide moieties attached to and pendent from the polymeric backbone. The resulting silicone grafted polymeric backbone is then subjected to the second reaction step of the process as described hereinbefore, thus producing graft copolymers comprising a plurality of nonsilicone-containing polymeric side chains in combination with one or more silicone-containing macromonomer grafts.

The optional silicone macromonomer is grafted to or polymerized into the polymeric backbone by any conventional or otherwise known method for making silicone graft copolymers. Most typically, these polymers are formed from the random copolymerization of vinyl or otherwise copolymerizable monomer units, some or all of which have attached organic halide moieties, and polysiloxane-containing macromonomer units containing a polymeric portion and a vinyl moiety copolymerizable with monomer units. Upon completion of polymerization, the siloxane polymeric portion of the macromonomer unit forms the polysiloxane side chains of the graft copolymer. The other copolymerizable monomer units and the vinyl portion of the macromonomer units form the polymeric backbone. The copolymerizable monomer and the polysiloxane-containing macromonomer can be selected from a wide variety of structures as long as the copolymer has the required properties described herein, including having the attached organic halide moieties which act as initiators in the second reaction step of the synthesis method herein.

Examples of related silicone graft copolymers, and methods of making them, are described in detail in U.S. Pat. No. 4,693,935, Mazurek, issued Sep. 15, 1987, U.S. Pat. No. 4,728,571, Clemens et al., issued Mar. 1, 1988, both of which are incorporated herein by reference. Additional silicone grafted polymers are also disclosed in EPO Application 90307528.1, published as EPO Application 0 408 311 A2 on Jan. 11, 1991, Hayama, et al., U.S. Pat. No. 5,061,481, issued Oct. 29, 1991, Suzuki et al., U.S. Pat. No. 5,106,609, Bolich et al., issued Apr. 21, 1992, U.S. Pat. No. 5,100,658, Bolich et al., issued Mar. 31, 1992, U.S. Pat. No. 5,100,657, Ansher-Jackson, et al., issued Mar. 31, 1992, U.S. Pat. No. 5,104,646, Bolich et al., issued Apr. 14, 1992, U.S. Ser. No. 07/758,319, Bolich et al, filed Aug. 27, 1991, and U.S. Ser. No. 07/758,320, Torgerson et al., filed Aug. 27, 1991, which descriptions are incorporated herein by reference.

The silicone graft copolymers made in accordance with the synthesis methods herein may comprise from zero to about 50%, preferably from about 2% to about 40%, and more preferably from about 10% to about 30%, polysiloxane macromonomer units by weight of the graft polymer.

The polysiloxane macromonomer units are copolymerizable with the other selected monomers for use in the first reaction step of the synthesis method, the polysiloxane macromonomers having a vinyl or other copolymerizable moiety for reaction with the other selected monomer. Either a single type of polysiloxane macromonomer unit or combinations of two or more polysiloxane macromonomer units can be used in the first reaction step. In this context, the term "copolymerizable" means that the polysiloxane macromonomers can be reacted with the other selected monomers, including the organic halide-containing monomers, in accordance with the first reaction step of the synthesis method herein, which results in the requisite polymeric backbone for use in the second reaction step of the synthesis method herein.

The polysiloxane macromonomers that are useful herein contain a polymeric portion and a copolymerizable moiety which is preferably an ethylenically unsaturated moiety. Typically, the preferred macromonomers are those that are endcapped with the vinyl moiety. By "endcapped" as used herein is meant that the vinyl moiety is at or near a terminal position of the macromonomer.

The polysiloxane macromonomers can be synthesized using a variety of conventional or otherwise known synthetic techniques familiar to the polymer chemist of ordinary skill in the art. Furthermore, these polysiloxane macromonomers can be synthesized starting from commercially available polymers. Typically, the weight average molecular weight of the polysiloxane macromonomer for use in the first reaction step is from about 1,000 grams/mole to about 50,000 grams/mole.

Polysiloxane macromonomers suitable for use herein include those which conform to the general formula:

$$X(Y)_nSi(R)_{3-m}Z_m$$

wherein X is a vinyl group copolymerizable with the vinyl monomer units; Y is a divalent linking group; each R is independently selected from the group consisting of hydrogen, hydroxyl, C1–C6 alkyl, C1–C6 alkoxy, C2–C6 alkylamino, styryl, phenyl, C1–C6 alkyl or alkoxy-substituted phenyl; Z is a monovalent siloxane polymeric moiety having a number average molecular weight of at least about 1000 and which is essentially unreactive under copolymerization conditions; n is an integer having a value of 0 or 1; and m is an integer having a value of from 1 to 3. The polysiloxane macromonomer has a weight average molecular weight from about 1,000 grams/mole to about 50,000 grams/mole, preferably from about 5,000 grams/mole to about 30,000 grams/mole, more preferably from about 8,000 grams/mole to about 25,000 grams/mole.

Preferably, the polysiloxane macromonomer has a formula selected from the following formulas I–III.

(I)

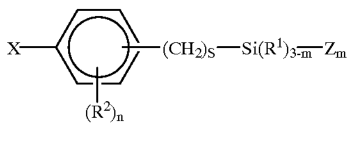

(II)

$$X—CH_2—(CH_2)_s—Si(R^1)_{3-m}—Z_m$$

(III)

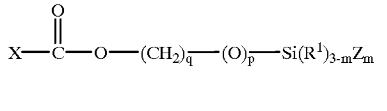

wherein s is an integer having a value of from 0 to 6; preferably 0, 1, or 2; more preferably 0 or 1; m is an integer having a value of from 1 to 3, preferably 1; p is an integer having a value of 0 or 1; q is an integer having a value of from 2 to 6; each $R^1$ is independently selected form the group consisting of hydrogen, hydroxyl, C1–C6 alkyl, C1–C6 alkoxy, C2–C6 alkylamino, phenyl, C1–C6 alkyl or alkoxy-substituted phenyl, preferably C1–C6 alkyl, or C1–C6 alkyl or alkoxy-substituted phenyl, more preferably C1–C6 alkyl, even more preferably methyl, $R^2$ is selected from the group consisting of C1–C6 alkyl or C1–C6 alkyl substituted phenyl, preferably methyl; n is an integer having a value of from 0 to 4, preferably 0 or 1, more preferably 0; X is

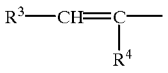

wherein $R^3$ is hydrogen or —COOH, preferably $R^3$ is hydrogen; $R^4$ is hydrogen, methyl or —$CH_2COOH$, preferably $R^4$ is methyl; Z is

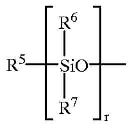

wherein $R^5$, $R^6$, and $R^7$, are independently selected from hydrogen, hydroxyl, C1–C6 alkyl, C1–C6 alkoxy, C2–C6 alkylamino, styryl, phenyl, C1–C6 alkyl or alkoxy-substituted phenyl, hydrogen or hydroxyl, preferably $R^5$, $R^6$, and $R^7$ are C1–C6 alkyls; more preferably methyl; and r is an integer having a value of from about 14 to about 700, preferably about 60 to about 400, and more preferably about 100 to about 170.

Personal Care Compositions

The graft polymers made in accordance with the methods herein are especially useful when used as film-forming polymers in personal care compositions. Such compositions comprise the graft polymers made in accordance with the methods herein in combination with a suitable liquid carrier to dissolve or disperse, preferably dissolve, the graft polymer in the personal care composition.

Personal care compositions containing polymers of the present invention include skin care compositions, styling or conditioning shampoo compositions, cosmetic compositions, or other similar compositions, many of which will further comprise one or more optional ingredients as described hereinafter. Preferred are hair care compositions such as conditioners, styling and/or conditioning shampoos, hair sprays, and styling mousses, tonics, gels or lotions. The film-forming graft polymer for use in such compositions, and which is made in accordance with the synthesis methods herein, provides the compositions with hair or skin conditioning performance or hair styling performance. The personal care compositions can be formulated as solids or liquids, single or multi-phase systems, emulsions, dispersions, solutions, gels, suspensions, or other formulation suitable for application to the skin or hair.

Personal care compositions containing polymers of the present invention comprise the graft polymers made in accordance with the methods herein, at concentrations effective to provide the desired film-forming properties. Such concentrations generally range from about 0.1% to about 15%, preferably from about 0.5% to about 15%, even more preferably from about 0.5% to about 8%, even more preferably from about 1% to about 8%, by weight of the personal care composition, wherein the concentration of the liquid carrier generally ranges from about 85% to about 99.9%, preferably from about 92% to about 99.5%, even more preferably from about 92% to about 99%, by weight of the personal care composition.

The personal care compositions, especially when formulated as hair styling compositions, may be dispensed as sprayed or atomized liquids from pump spray or aerosol canisters. The aerosolized compositions comprise one or more conventional or otherwise known aerosol propellants. Suitable propellants include any liquifiable gas known or otherwise effective for use in this manner, examples of which include volatile hydrocarbon propellants such as liquified lower hydrocarbons having 3 or 4 carbon atoms such as propane, butane, isobutane, or combinations thereof. Other suitable propellants include hydrofluorocarbons such as 1,2-difluoroethane, and other propellants such as dimethylether, nitrogen, carbon dioxide, nitrous oxide, atmospheric gas, and combinations thereof. Preferred are hydrocarbon propellants, particularly isobutane when used alone or in combination with other hydrocarbon propellants. Propellant concentrations should be sufficient to provide the desired delivery or application of the personal care composition to the hair or skin, which concentrations typically range from about 10% to about 60%, preferably from about 15% to about 50%, by weight of the composition.

Pressurized aerosol dispensers can also be used where the propellant is separated from contact with the hair styling composition, an example of which would be a two compartment canister available from the American National Can Corp. under the trade name SEPRO. Other suitable aerosol dispensers are those characterized by the propellant being compressed air which can be filled into the dispenser by means of a pump or equivalent device prior to use. Such dispensers are described in U.S. Pat. No. 4,077,441, U.S. Pat. No. 4,077,441 and U.S. Ser. No. 07/839,648, which descriptions are incorporated herein by reference. Conventional non-aerosol pump spray dispensers or atomizers are also suitable for use herein.

A) Hydrophilic graft polymer compositions

Personal care compositions containing polymers of the present invention preferably comprise a hydrophilic graft polymer made in accordance with the synthesis methods herein, and which is used in combination with a hydrophilic or water soluble or miscible liquid carrier suitable for solubilizing or dispersing the hydrophilic graft polymer in the personal care composition. These preferred compositions are especially useful when used as hair spray or other hair styling compositions.

Hydrophilic liquid carriers suitable for use herein include, but are not limited to, water, ethanol, n-propanol, isopropanol, and combinations thereof, preferably a combination of an alcohol and water wherein the water content of the composition ranges from about 0.5% to about 99%, preferably from about 0.5% to about 50%, by weight of the composition, and the alcohol content ranges from about 0.5% to about 99%, preferably from about 50% to about 95%, by weight of the composition.

The hydrophilic graft polymers preferably have at least two distinct glass transition temperatures (Tg), the first of which is associated with the polymeric backbone and the second of which is associated with the plurality of polymeric side chains attached thereto. The polymeric backbone preferably has a Tg value of less than about 35° C., more preferably less than about 25° C., even more preferably less than about 10° C., wherein the plurality of polymeric side chains have a Tg value preferably greater than about 50° C., more preferably greater than about 60° C., even more preferably greater than about 70° C.

Other suitable hydrophilic graft polymers made in accordance with the methods herein include those having a Tg value for the polymeric backbone of greater than about 30° C., more preferably greater than about 40° C., even more preferably greater than about 50° C., wherein the plurality of polymeric side chains have a Tg value preferably of less than about 10° C., more preferably less than about 0° C., even more preferably less than about −20° C.

These personal care compositions, especially when formulated as hair spray compositions, preferably contain reduced concentrations of volatile organic compounds, including volatile organic solvents. In this context, the volatile organic compounds or solvents are those organic compounds or solvents that contain less than 12 carbon atoms or have a vapor pressure greater than 0.1 mm of mercury. Water concentrations in these preferred compositions are typically at least about 10% by weight of the composition, preferably from about 10% to about 50% by weight of the composition, wherein the concentration of the volatile organic compound or solvent is typically less than about 90%, preferably from about 20% to about 80%, more preferably from about 40% to about 70%, even more preferably from about 40% to about 60%, by weight of the composition.

B) Hydrophobic graft polymer compositions

Another embodiment of the personal care compositions of the present invention are those which comprise a hydrophobic graft polymer made in accordance with the synthesis methods herein, in combination with a hydrophobic or water insoluble liquid carrier suitable for solubilizing or dispersing or otherwise carrying the hydrophobic graft polymer in the personal care composition. These embodiments are especially useful when used as hair or skin conditioning compositions, some nonlimiting examples of which include skin care compositions, conditioning shampoos, and hair conditioners.

Suitable hydrophobic liquid carriers for the hydrophobic graft polymers include hydrophobic, volatile, liquids such as volatile branched chain hydrocarbons, silicones and combinations thereof. The concentration of such liquid carriers in the composition preferably range from about 0.1% to about 75%, more preferably from about 0.2% to about 25%, and even more preferably from about 0.5% to about 15%, by weight of the composition, wherein the weight ratio of hydrophobic graft polymer to the hydrophobic liquid carrier is generally from about 1:100 to about 5:1, preferably from about 1:10 to about 1:1, more preferably from about 1:8 to about 2:3.

The hydrophobic liquid carrier is preferably a volatile liquid which exhibits a significant vapor pressure at ambient conditions (e.g., 1 atmosphere, 25° C.). In this context, the term "volatile" refers to solvents or liquid carriers having a boiling point at one atmosphere of 260° C. or less, preferably 250° C. or less, more preferably 230° C. or less, most preferably 225° C. or less. In addition, the boiling point of the hydrophobic liquid carrier will generally be at least about 50° C., preferably at least about 100° C. The term "nonvolatile" as used in this context refers to solvents or liquid carriers which have a boiling point at one atmosphere of greater than 260° C.

The hydrophobic graft polymer is preferably soluble in the selected hydrophobic liquid carrier. In this context, the term "soluble" refers to the solubility of the hydrophobic graft polymer in the hydrophobic liquid carrier at 25° C. at a concentration of 0.1%, preferably at 1%, more preferably at 5%, most preferably at 15%, by weight of the hydrophobic liquid carrier.

Preferred hydrophobic liquid carriers include hydrophobic, volatile, branched chain hydrocarbons, preferably saturated hydrocarbons, which contain from about 10 to about 16, preferably from about 12 to about 16, most preferably from about 12 to about 14, carbon atoms. Examples of such preferred branched chain hydrocarbons include isoparaffins of the above chain sizes. Isoparaffins are commercially available from Exxon Chemical Co.; examples include Isopar™ H and K ($C_{11}$–$C_{12}$ isoparaffins), and Isopar™ L ($C_{11}$–$C_{13}$ isoparaffins). Other suitable branched chain hydrocarbons are isododecane and isohexadecane. Isododecane is preferred and is commercially available from Preperse, Inc. (South Plainfield, N.J., USA) as Permethyl™ 99A.

Preferred hydrophobic silicone carriers include hydrophobic, volatile siloxanes (such as phenyl pentamethyl disiloxane, phenylethyl pentamethyl disiloxane, hexamethyl disiloxane, methoxypropyl heptamethyl cyclotetrasiloxane, chloropropyl pentamethyl disiloxane, hydroxypropyl pentamethyl disiloxane, cyclomethicones, including octamethyl cyclotetrasiloxane and decamethyl cyclopentasiloxane), and mixtures thereof. Preferred hydrophobic silicone solvents are cyclomethicones, more preferably octamethyl cyclotetrasiloxane and decamethyl cyclopentasiloxane.

It is understood that the hydrophobic liquid carriers can be used in combination with the hydrophilic liquid carriers in the personal care compositions, and that the hydrophobic graft polymers can likewise be used in combination with the hydrophilic graft polymers in the personal care composition. Such combinations are suitable for use in the personal care composition provided that they are physically and chemically compatible with the selected ingredients in the composition, and do not otherwise substantially and unduly impair product performance.

Optional Ingredients

The personal care compositions described herein may further comprise one or more optional ingredients known or otherwise effective for use in hair styling compositions or other personal care compositions. These optional ingredients may be used to improve or otherwise modify aesthetics, performance or stability of the hair styling compositions. Concentrations of such options ingredients will vary with the type of material added and its intended performance, but will typically and collectively range from about 0.005% to about 50%, more typically from about 0.05% to about 30% by weight of the composition.

Plasticizers for the graft copolymer are especially useful in the personal care compositions herein. Suitable plasticizers include any known or otherwise effective plasticizer suitable for use in hair care or other personal care compositions, nonlimiting examples of which include glycerin, diisobutyl adipate, butyl stearate, propylene glycol, tri-$C_2$–$C_8$ alkyl citrates, including triethyl citrate and tripropyl, -butyl, -pentyl, etc., analogs of triethyl citrate. Triethyl citrate is preferred.

Plasticizers are typically used at levels of from about 0.01% to about 10%, by weight of the composition, preferably from about 0.05% to about 3%, more preferably from about 0.05% to about 1%. Preferably, the weight ratio of graft polymer to the plasticizer is from about 1:1 to about 40:1, preferably from about 2:1 to about 30:1, more preferably from about 3:1 to about 25:1.

Other optional ingredients include an effective amount of a non-surface active ionic strength modifier system for reducing the viscosity of the personal care composition, especially when formulated as a hair spray composition. Preferred concentrations range from at least about 0.01%, by weight of the composition. The upper limit is dependent upon the maximum amount of the ionic strength modifiers that can be present in the particular compositions hereof such that the hair setting resin remains solubilized or dispersed. As will be understood by those skilled in the art, as the ionic strength of the composition is increased, the resin will eventually fall out of solution, or otherwise no longer remain solubilized or dispersed in the hydrophilic liquid carrier. The upper limit of the ionic strength modifier system level will vary depending upon the particular ionic strength modifiers, liquid vehicle, resin, and other ingredients present in the composition. Thus, for example, the maximum amount of the ionic strength modifiers that can be used will tend to be lower for compositions with liquid vehicles containing less water, compared to compositions with more water. Concentrations of the optional ionic strength modifier are typically range from about 0.01% to about 4%, preferably from about 0.01% to about 2%, more preferably from about 0.01% to about 0.1%, by weight of the composition The optional ionic strength modifier system comprises a mixture of monomeric cations and anions. The ions of the ionic strength modifier system hereof are non-surface active, i.e. they do not significantly reduce surface tension. For purposes hereof, non-surface active shall mean the ions, which at a 0.5% aqueous solution concentration, reduce surface tension by no more than 5.0 dynes/$cm^2$. Generally, the ions of the ionic strength modifier system hereof will be characterized by having, at maximum, four or less carbon atoms per charge, preferably two or less carbon atoms, in any aliphatic chain or straight or branched chain organic heterochain.

The optional ionic strength modifier system comprises monomeric ions of the type which are products of acid-base reactions. Thus, basic and acidic ions $OH^-$and $H^+$do not constitute part of the ionic strength modifier system hereof, although they may be present in the composition. The ions hereof are incorporated into the composition in a form such that they can exist in the composition as free ions, i.e., in dissociated form. It is not necessary that all of the ions added exist in the composition as free ions, but must be at least partially soluble or dissociated in the composition. The ionic strength modifiers can be incorporated into the hair styling compositions, for example, by addition of soluble salts, or by addition of mixtures of acids and bases, or by a combination thereof. It is a necessary aspect of the invention that both anions and cations of the ionic strength modifier system be included in the composition.

Nonlimiting examples of suitable optional cations for use in the compositions are alkali metals, such as lithium, sodium, and potassium, and alkaline-earth metals, such as magnesium, calcium, and strontium. Preferred of the divalent cations is magnesium. Preferred monovalent metal ions are lithium, sodium, and potassium, more preferably sodium and potassium. Suitable means of addition to the compositions hereof include, for example, addition as bases, e.g., hydroxides, sodium hydroxide and potassium hydroxide, and such as salts that are soluble in the liquid carrier, e.g. salts of monomeric anions such as those described below. Other nonlimiting examples of suitable cations include organic ions, such as quaternary ammonium ions and cationic amines, such as ammonium mono-, di-, and triethanolamines, triethylamine, morpholine, aminomethylpropanol (AMP), aminoethylpropanediol, etc. Ammonium and the amines are preferably provided in the forms of salts, such as hydrochloride salts.

Monomeric anions that can be used include halogen ions, such as chloride, fluoride, bromide, and iodide, particularly chloride, sulfate, ethyl sulfate, methyl sulfate, cyclohexyl sulfamate, thiosulfate, toluene sulfonate, xylene sulfonate, citrate, nitrate, bicarbonate, adipate, succinate, saccharinate, benzoate, lactate, borate, isethionate, tartrate, and other monomeric anions that can exist in dissociated form in the hair styling composition. The anions can be added to the compositions hereof, for example, in the form of acids or salts which are at least partially soluble in the liquid vehicle, e.g., sodium or potassium salts of acetate, citrate, nitrate, chloride, sulfate, etc. Preferably, such salts are entirely soluble in the vehicle.

The use of optional ionic strength modifiers are especially useful in reduced volatile organic solvent compositions.

Other optional ingredients include surfactants (which may be anionic, cationic, amphoteric, or zwitterionic and which include fluorinated surfactants and silicone copolyols), propellants, hair conditioning agents (e.g., silicone fluids, fatty esters, fatty alcohols, long chain hydrocarbons, cationic surfactants, etc.); emollients; lubricants and penetrants such as various lanolin compounds; protein hydrolysates and other protein derivatives; ethylene adducts and polyoxyethylene cholesterol; dyes, tints, bleaches, reducing agents and other colorants; pH adjusting agents; sunscreens; preservatives; thickening agents (e.g. polymeric thickeners, such as xanthan gum); and perfume.

Method of Use

Personal care compositions containing polymers of the present invention are used in conventional ways to provide the desired personal care benefit. For hair spray or other hair styling compositions, the composition is used in a conventional way to provided the desired hair styling/holding benefits of the present invention, which typically involves application of an effective amount of the composition to dry, slightly damp, or wet hair before and/or after the hair is arranged to a desired style. The composition is then dried or allowed to dry onto the applied surface.

The term “effective amount” as used in this context means an amount of the personal care composition or hair styling composition sufficient to provide the desired benefit. In the case of hair spray and other hair styling compositions, an effective amount of the composition is applied to the hair to provide the hold and style benefits desired considering the length and texture of the hair. In general, from about 0.5 g to about 30 g of such hair spray or other hair styling composition will be applied to the hair, depending upon the particular product formulation, dispenser type, length of hair, type of hair style, and so forth.

EXAMPLES

The following non-limiting examples illustrate specific embodiments of the synthetic method of the present invention, graft polymers made in accordance with such a method, and hair styling and other personal care compositions comprising these graft polymers. It is understood, however, that various additions or modifications of the specific exemplified embodiments can be made without departing from the spirit and scope of the invention. It is intended to cover, in the appended claims, all such modifications that are within the scope of the subject invention.

Example 1

The hydrophilic graft polymers 1.1 and 1.2 described in the following example are prepared in accordance with the synthesis methods of the present invention. Specific embodiments of the synthesis method of the present invention are described for each of the hydrophilic graft polymers.

Graft Polymer 1.1

Poly(2-methoxyethyl acrylate-co-methacrylic acid-co-tert-butyl acrylate)-graft-poly(styrene-co-methacrylic acid)

Into an argon purged round-bottomed-flask equipped with mechanical stirring and a reflux condenser, is added butyl acetate (1 L), trimethylsilylmethacrylate (18.4 g, 0.116 mole), tert-butylacrylate (27.2 g, 0.212 mole), 2-methoxyethyl acrylate (31.4 g, 0.241 mole), and chloromethyl styrene (0.4 g, 0.003 mole). The solution is heated to 60° C. then initiated with AIBN (azobisisobutyronitrile) (0 g, 0.006 mole) and allowed to undergo free radical polymerization for 10 hours. The resulting solution is then heated to 100° C. and allowed to cool. When the solution reaches ambient temperature, trimethylsilylmethacrylate (22.0 g, 0.139 mole), styrene (18.0 g, 0.173 mole), 2,2'-dipyridyl (1.4 g, 0.009 mole), and Cu(I)Cl (0.3 g, 0.003 mole) are added. The solution is then heated to 120° C. with stirring for 6 hours. The solution is then cooled to ambient temperature and catalyst is removed via vacuum filtration. The filtrate is diluted with acetone (200 ml) and water (10 ml) and stirred for 2 hours. The resulting solution is precipitated into hexanes and the graft polymer collected and dried.

Graft Polymer 1.2

Poly(2-methoxyethyl acrylate-co-methacrylic acid-co-tert-butyl acrylate)-graft-[poly(styrene-co-methacrylic acid); poly (dimethylsiloxane)]

Into an argon purged round-bottomed-flask equipped with mechanical stirring and a reflux condenser, is added butyl acetate (1 L), trimethylsilyl methacrylate (18.4 g, 0.116 mole), tert-butylacrylate (27.2 g, 0.212 mole), 2-methoxyethyl acrylate (26.4 g, 0.203 mole), polydimethylsiloxane macromonomer (molecular weight 10,000) (available from Chisso Corp., Tokyo, Japan) (5 g), and chloromethyl styrene (0.4 g, 0.003 mole). The solution is heated to 60° C. then initiated with AIBN (1.0 g, 0.006 mole) and allowed to undergo free radical polymerization for 10 hours. The resulting solution is then heated to 100° C. then allowed to cool. When solution reaches ambient temperature, trimethylsilylmethacrylate (22.0 g, 0.139 mole), styrene (18.0 g, 0.173 mole), 2,2'-dipyridyl (1.4 g, 0.009 mole), and Cu(I)Cl (0.3 g, 0.003 mole) are added. The solution is heated to 120° C. with stirring for 6 h. The solution is then cooled to ambient temperature and catalyst is removed via vacuum filtration. Filtrate is diluted with acetone (200 ml) and water (10 ml) and stirred for 2 hours. The resulting solution is precipitated into hexanes and the graft polymer collected and dried.

Example 2

The hydrophobic graft polymer 2.0 described in the following example is prepared in accordance with the synthesis methods of the present invention. Specific embodiments of the synthesis method of the present invention are described for each of the hydrophobic graft polymers.

Graft Polymer 2.0

Poly(tert-butyl acrylate-co-2etylhexyl methacrylate)-graft-poly(n-butyl acrylate)

Into an argon purged round-bottomed-flask equipped with mechanical stirring and a reflux condenser, is added butyl acetate (1 L), tert-butyl acrylate (54 g, 0.417 mole), 2-ethylhexyl methacrylate (10 g, 0.050 mole), and chloromethyl styrene (6 g, 0.039 mole). The solution is heated to 60° C. and then initiated with AIBN (0.6 g, 0.004 mole) and allowed to undergo free radical polymerization for 12 hours. The resulting solution is the heated to 100° C. then allowed to cool. When solution reaches ambient temperature, n-butyl acrylate (30 g, 0.211 mole), 2,2'-dipyridyl (18.3 g, 0.117 mole), and Cu(I)Cl (3.9 g, 0.039 mole) are added. The solution is heated to 120° C. with stirring for 6 hours. The solution is then cooled to ambient temperature and catalyst is removed via vacuum filtration. The filtrate is diluted with acetone (200 ml) and water (10 ml) and stirred for 2 hours. The resulting solution is precipitated into hexanes and the graft polymer collected and dried.

Examples 3–10

The following Examples 3–10 represent nonaerosol hair spray embodiments of the compositions of the present invention.

| Component (wt %) | Example No 3 | 4 | 5 | 6 | 7 | 8 | 9 | 10 |
|---|---|---|---|---|---|---|---|---|
| Graft copolymer 1.1 | 4.00 | 5.00 | 6.00 | 4.00 | — | — | — | — |
| Graft copolymer 1.2 | — | — | — | — | 3.00 | 3.50 | 2.50 | 4.00 |
| Isododecane[1] | 1.00 | — | — | — | — | 1.0 | 2.0 | — |
| Diisobutyl adipate | 0.40 | — | 0.90 | 0.55 | — | — | — | 0.40 |
| Sodium hydroxide[2] | 0.96 | 1.20 | 1.44 | — | — | 1.20 | — | 1.35 |
| Potassium hydroxide[3] | — | — | — | 1.21 | 1.00 | — | 0.70 | — |
| Perfume | 0.10 | 0.10 | 0.10 | 0.10 | 0.10 | 0.15 | 0.10 | 0.15 |
| Sodium Benzoate | — | — | — | — | 0.10 | 0.10 | — | 0.10 |
| Ethanol[4] | 76.54 | 71.95 | 81.56 | 71.25 | 79.40 | 69.26 | 78.00 | 55.00 |
| Water | QS100 | QS100 | QS100 | QS100 | QS100 | QS100 | QS100 | QS100 |

[1]PERMETHYL 99A, from Presperse, Inc., South Plainfield, NJ, USA.
[2]Sodium hydroxide is 30% active.
[3]Potassium hydroxide is 45% active.
[4]SDA 40 (100% ethanol).

Examples 11–16

The following Examples 11–16 represent aerosol hair spray embodiments of the compositions of the present invention.

| Component (wt %) | Example No. 11 | 12 | 13 | 14 | 15 | 16 |
|---|---|---|---|---|---|---|
| Graft copolymer 1.1 | 5.00 | 4.00 | 3.50 | — | — | — |
| Graft copolymer 1.2 | — | — | — | 4.00 | 3.00 | 4.00 |
| Isododecane[1] | 0.50 | — | — | — | — | 0.50 |
| Triethyl citrate[2] | — | — | 0.21 | — | — | — |

-continued

| Component | Example No. | | | | | |
|---|---|---|---|---|---|---|
| (wt %) | 11 | 12 | 13 | 14 | 15 | 16 |
| Diisobutyl adipate | 0.70 | 0.45 | — | 0.40 | 0.25 | 0.35 |
| Propylene glycol | — | — | 0.30 | — | — | — |
| Sodium hydroxide[3] | 1.00 | — | — | — | 1.0 | — |
| Potassium hydroxide[4] | — | 0.94 | 1.20 | 1.04 | — | 1.20 |
| Perfume | 0.10 | 0.10 | 0.10 | 0.10 | 0.10 | 0.10 |
| Sodium Benzoate | 0.10 | 0.10 | — | 0.10 | 0.20 | — |
| Ethanol[5] | 56.69 | 57.42 | 72.0 | 50.0 | 30.00 | 54.5 |
| Propellant - isobutane | — | — | 7.02 | 15.00 | 10.00 | — |
| Propellant - n-butane | 10.00 | — | — | — | — | — |
| Propellant - dimethyl ether[6] | 10.00 | — | — | 15.00 | 15.00 | — |
| Propellant - Hydrofluoro-carbon 152a[7] | — | 25.0 | 15.98 | — | — | 32.32 |
| Water | QS100 | QS100 | QS100 | QS100 | QS100 | QS100 |

[1]PERMETRYL 99A, from Presperse, Jnc., South Plainfield, NJ, USA.
[2]CITROFLEX-2, from Morflex, Inc., Greensboro, NC, USA.
[3]Sodium hydroxide is 30% active.
[4]Potassium hydroxide is 45% active.
[5]SDA 40 (100% ethanol).
[6]DYMEL - A, from Dupont.
[7]DYMEL-152a, from Dupont.

Each of the exemplified personal care compositions (Examples 3–16) are hair spray or hair styling embodiments of the compositions of the present invention, and comprise graft polymer as a styling or film-forming polymer made in accordance with the synthetic methods of the present invention. Each of the compositions may be formulated by conventional or otherwise known formulation and mixing techniques. For example, each of the graft polymers is first mixed with the ethanol, neutralizing the polymer with sodium or potassium hydroxide, then adding sequentially (as applicable) with mixing, isododecane, plasticizer, perfume, and water. If sodium benzoate is used, it is added after water addition. Most preferably a premix of water and sodium benzoate is made and then added after the main water addition. Propellants for aerosol compositions are charged to conventional aerosol containers after the remainder of the prepared composition has been added.

Example 17

The following represents a hair styling gel embodiment of the composition of the present invention.

| Ingredients | Weight % |
|---|---|
| Graft copolymer 1.2 | 2.50 |
| Water | QS 100% |
| Carbomer 940 | 0.50 |
| Sodium Hydroxide Solution (30% by weight) | 0.80 |
| Panthenol | 0.05 |
| Polysorbate 80 | 0.20 |
| Perfume | 0.20 |

This product is prepared by dispersing graft copolymer and carbomer 940 in water and adding sodium hydroxide. The mixture is stirred for about 0.5 hour before adding the remaining ingredients.

Example 18

The following represents a spray-on gel embodiment of the composition of the present invention.

| Ingredients | Weight % |
|---|---|
| Water | Q.S. to 100% |
| Ethanol | 15.00 |
| Panthenol | 0.05 |
| Potassium Hydroxide Solution (45% by weight) | 0.50 |
| Perfume | 0.20 |
| Graft copolymer 1.1 | 2.00 |

This composition is prepared by dissolving the graft copolymer 1.1 in ethanol and then adding water and potassium hydroxide solution to facilitate the incorporation of the copolymer into the solvent. The mixture is stirred for about 0.5 hour before adding the remaining ingredients.

Example 19

The following represents a hair styling mousse embodiment of the composition of the present invention.

| Ingredients | Weight % |
|---|---|
| Water | Q.S. to 100% |
| Lauramine Oxide | 0.20 |
| Panthenol | 0.05 |
| Perfume | 0.05 |
| Copolymer 1.2 | 3.00 |
| Sodium Hydroxide Solution (30% by weight) | 1.00 |
| Isobutane | 7.00 |

This composition is prepared by dissolving the graft copolymer 1.2 in water and then adding sodium hydroxide solution with mixing for about 0.5 hour. The other ingredients, except isobutane, are added and mixed for an additional 10 minutes. Aluminum aerosol cans are then filled with 93 parts of this batch, affixed with a valve which is crimped into position, and lastly pressure filled with 7 parts Isobutane. This composition is useful for application to the hair to provide conditioning, styling and hold.

Example 20

The following example represents a topical sun screen embodiment of the composition of the present invention.

| Ingredients | Weight % |
|---|---|
| Water | QS100 |
| Carbomer 1342[1] | 0.16 |
| Octyl Methoxycinnamate | 0.50 |
| Dimethicone copolyol | 0.10 |
| Tocopheryl Acetate | 0.10 |
| Sodium Hydroxide (30% sol. by weight) | 1.50 |
| Ethanol | 40.00 |
| Copolymer 1.2 | 4.00 |

[1]Available as Carbopol ®1342 from B.F. Goodrich.

The water, ethanol, sodium hydroxide solution and polymer 4 are mixed for one half hour. The remaining ingredients are added and mixed for an additional half hour.

This composition is prepared by combining and mixing the graft copolymer 1.2 and water, ethanol, sodium hydroxide solution. The remaining ingredients are then added to the mixture.

Example 21

The following example represents a topical skin care embodiment of the composition of the present invention.

| Ingredients | Weight % |
|---|---|
| Graft copolymer 1.2 | 2.00 |
| Water | Q.S. to 100% |
| Ethanol (SDA 40) | 40.00 |
| Carbomer 940 | 0.75 |
| Sodium Hydroxide Solution (30% by weight) | 0.90 |
| Salicylic Acid | 2.00 |

The composition is prepared by mixing water, ethanol, graft copolymer, and carbomer together for about 10 minutes. The remaining ingredients are added and the mixture is stirred for an additional 30 minutes. This composition is useful for application to the skin to provide improved water resistance and is useful in treating acne.

Example 22

The following example represents a nail polish embodiment of the composition of the present invention. The composition is prepared by combining and mixing all of the listed ingredients until uniformly dispersed throughout the composition.

| Ingredients | Weight % |
|---|---|
| Graft copolymer 1.1 | 15.00 |
| Ethanol | 42.00 |
| Acetone | 40.00 |
| NaOH soln., 30% | 3.00 |

Example 23

The following example represents a topical skin care embodiment of the composition of the present invention. The topical composition is intended for use in treating, preventing or otherwise reducing the appearance of wrinkles on human skin. The composition is prepared by combining and mixing all of the listed ingredients until uniformly dispersed throughout the composition.

| Ingredients | Weight % |
|---|---|
| Graft copolymer 1.1 | 6.00 |
| NaOH soln., 30% | 2.10 |
| DRO Water (purified by double reverse osmosis) | q.s. |

Example 24

The following example represents a hair styling lotion embodiment of the composition of the present invention. The graft copolymer is dissolved in ethanol and then added and mixed with the remaining ingredients until uniformly dispersed throughout the composition.

| Ingredients | Weight % |
|---|---|
| Graft copolymer 1.1 | 4.00 |
| Natrosol 250HH[1] | 0.50 |
| NaOH soln., 30% | 1.35 |
| Kathon CG | 0.03 |
| Ethanol | 8.00 |
| DRO water | q.s. |

[1]Natrosol 250HH-Hydroxyethylcellulose offered by Aqualon.

Example 25

The following example represents an aftershave embodiment of the composition of the present invention. The composition is prepared by combining and mixing all of the listed ingredients until uniformly dispersed throughout the composition.

| Ingredients | Weight % |
|---|---|
| Graft copolymer 1.2 | 2.00 |
| NaOH soln., 30% | 0.60 |
| Ethanol | 50.00 |
| Perfume | 0.20 |
| Menthol | 0.20 |
| DRO water | q.s. |

Examples 26–28

The following examples represent hair styling/conditioning rinse embodiments of the compositions of the present invention.

| | Example No. | | |
|---|---|---|---|
| Composition | 26 | 27 | 28 |
| Conditioner Premix | | | |
| Water | q.s. | q.s. | q.s. |
| Citric Acid | 0.02 | 0.02 | 0.02 |
| Sodium Citrate | 0.09 | 0.09 | 0.10 |
| Cetyl Alcohol | 0.12 | 0.12 | 0.12 |
| Stearyl Alcohol | 0.08 | 0.08 | 0.08 |
| Natrosol Plus CS Grade D-67[1] | 1.02 | 1.00 | 0.99 |
| Xanthan Gum[2] | 0.25 | 0.25 | 0.25 |
| Styling Polymer Premix | | | |
| Graft polymer 2.0 | 1.75 | 1.75 | 1.75 |
| Peimethyl 99A | 8.54 | 8.54 | 8.54 |
| Trimethylsiloxysilicate | 0.11 | 0.11 | 0.11 |
| Kathon CG | 0.03 | 0.03 | 0.03 |
| Perfume | 0.33 | 0.33 | 0.33 |
| Silicone Premix | | | |
| DRO Water | 9.48 | 9.48 | 8.57 |
| Adogen 470[4] | 0.70 | 0.60 | 0.93 |
| Adogen 471[5] | 0.05 | 0.15 | 0.07 |
| Decamethyl cyclopentasiloxane/ Polydimethyl Siloxane Gum[3] | 1.67 | 1.67 | 2.33 |
| Triethylsilyl Amodimethicone (Dow Corning Q2-8220) | 0.10 | 0.10 | 0.10 |
| Surfactant Premix | | | |
| DRO Water | 5.70 | 5.70 | 5.70 |
| Stearalkonium Chloride | 0.30 | 0.30 | 0.30 |

[1]Hydrophobically modified hydroxyethyl cellulose from Aqualon Corp.
[2]Readily dispersible xantham gum
[3]SE-76 gum available From General Electric
[4]Ditallow dimethyl ammonium chloride, Sherex Chemical Co., Dublin, Ohio, USA; 75% aqueous solution
[5]Tallow trimethyl ammonium chloride, Sherex Chemical Co.; 50% aqueous solution.

Each of the exemplified compositions are prepared as follows. A silicone premix is prepared by combining and mixing (in a separate vessel) water, Adogen 470 and Adogen 471 at 85° C. Cool to 71° C. and add the silicone gum/decamethyl cyclopentasiloxane solution and amodimethicone and mix until homogeneous. Cool to 38° C. while using a homogenizer (such as Tekmar). Prepare the surfactant premix by combining and mixing (in a second and separate vessel) water and Stearalkonium Chloride at 38° C. Prepare the conditioner premix by combining and mixing (in a third and separate vessel) DRO water heated to 71° C., citric acid, sodium citrate, cetyl alcohol, stearyl alcohol and Natrosol Plus CS grade D-67, and until uniformly dispersed, and then add xanthan gum and mix until uniformly dispersed. Prepare the styling polymer premix by combining and mixing the graft polymer, permethyl 99A, and Trimethylsiloxysilicate until a uniform mixture is obtained.

Combine and mix the styling polymer premix, Kathon CG and perfume until homogeneous. Further dispersed with an in-line homogenizer (such as Tekmar homogenizer) and then cool the mixture to 38° C. Complete the conditioner by adding the conditioner premix, the silicone premix and the surfactant premix at 38° C. Mix until homogeneous, then cool the composition to 25° C.

When the compositions defined in Examples 26–28 are applied to hair in the conventional manner, they provide effective hair conditioning and styling/hold benefits without leaving the hair with a sticky/stiff feel.

Example 29

| Polymer Premix with added Drying Aid Ingredients | Weight % |
|---|---|
| Graft copolymer 2.0 | 16.83 |
| Permethyl 99A | 82.17 |
| Trimethylsiloxysilicate | 1.00 |

This polymer premix is prepared by adding the graft copolymer to the solvents while mixing. The mixture is heated to between 80° C. and 84° C. in a covered vessel while mixing, and then cooled to between 23° C. and 27° C. before adding trimethylsiloxysilicate while mixing.

Example 30

| Polymer Premix with added Drying Aid Ingredients | Weight % |
|---|---|
| Graft copolymer 2.0 | 15.00 |
| Isododecane | 83.50 |
| Polydimethylsiloxane[2] | 1.50 |

[2]Polydimethylsiloxane, Dow Corning, Dow Corning 200 Fluid (20 csk)

This polymer premix is prepared by adding the graft copolymer to the solvents while mixing. The mixture is heated to between 80° C. and 84° C. in a covered vessel while mixing, and then cooled to between 23° C. and 27° C. before adding trimethylsiloxysilicate while mixing.

Example 31

The following example represents a hair conditioning embodiment of the composition of the present invention.

-continued

| Ingredient | Weight % A | Weight % B |
|---|---|---|
| Styling Agent Premix | | |
| Graft copolymer Premix of Example 30 | 10.00 | 10.00 |
| Silicone Premix | | |
| Silicone gum, GE SE76[2] | 0.30 | 0.30 |
| Octamethyl cyclotetrasiloxane | 1.70 | 1.70 |
| Main Mix | | |
| Water | QS100 | QS100 |
| Cetyl Alcohol | 1.00 | — |
| Quaternium 18[3] | 0.85 | 0.85 |
| Stearyl Alcohol | 0.70 | — |
| Hydroxethyl Cellulose | 0.50 | — |
| Cetyl Hydroxyethyl Cellulose[4] | — | 1.25 |
| Ceteareth-20 | 0.35 | — |
| Fragrance | 0.20 | 0.20 |
| Dimethicone copolyol | 0.20 | — |
| Citric Acid | 0.13 | 0.13 |
| Methylchloroisothiazolinone (and) methylisothiazolinone | 0.04 | 0.04 |
| Sodium Chloride | 0.01 | 0.01 |
| Xanthan Gum | — | 0.20 |

Each of the compositions is prepared by comixing all the Main Mix ingredients, heating the resulting mixture to about 60° C. with mixing. The heated mixture is then cooled to about 45° C. with colloid milling (Example A) or mixing (Example B). At this temperature, the two premixes are added separately with moderate agitation and the resulting conditioner is allowed to cool to room temperature. This composition is useful as a rinse off hair conditioner.

[2]Commercially available from General Electric.

[3]Dimethyl Di(Hydrogenated Tallow) Ammonium Chloride

[4]Commercially available as Polysurf D-67 from Aqualon.

Example 32

The following example represent a shampoo embodiment of the composition of the present invention.

| Ingredients | Weight % |
|---|---|
| Styling Agent | |
| Copolymer Premix from Example 30 | 15.00 |
| Premix | |
| Silicone gum | 0.50 |
| Dimethicone, 350 cs fluid | 0.50 |
| Main Mix | |
| Water | QS100 |
| Ammonium lauryl sulfate | 11.00 |
| Cocamide MEA | 2.00 |
| Ethylene glycol distearate | 1.00 |
| Xanthan Gum | 1.20 |
| Methylchloroisothiazolinone (and) methylisothiazolinone | 0.04 |
| Citric Acid to pH 4.5 as needed | |

The Main Mix is prepared by first dissolving xanthan gum in water with conventional mixing. The remaining Main Mix ingredients are added and the Main Mix is heated to 150° F. with agitation for about 0.5 hour. The Styling Agent and the Premix are then added sequentially with about 10 minutes of agitation between additions, and the entire mixture is stirred while the batch is cooled to room temperature. For varied particle size, the Styling Agent and Premix can be added at different times using either or both high shear mixing (high speed dispersator) or normal agitation. This shampoo composition is useful for cleansing the hair and for providing a styling benefit.

What is claimed is:

1. A method of making graft polymers, which process comprises the steps of:

(a) reacting copolymerizable monomers to form an organic polymeric backbone having a weight average molecular weight of from about 15,000 grams/mole to about 9,800,000 grams/mole and a plurality of organic halide moieties covalently bonded to the polymeric backbone and pendant from the polymeric backbone and then without a separate purification or isolation step;

(b) reacting copolymerizable monomers with the organic halide moieties of the polymeric backbone by atom transfer free radical polymerization in the presence of a catalytic amount of a Cu(I) salt complexed to a ligand suitable for solubilizing the salt in the reaction mixture to form a plurality of polymeric side chains covalently bonded to the polymeric backbone and pendant from the polymeric backbone, the polymeric side chains having an average molecular weight of from about 500 grams/mole to about 200,000 grams/mole;

wherein the polymeric backbone and the plurality of polymeric side chains form graft polymers having a weight average molecular weight of from about 16,000 grams/mole to about 10,000,000 grams/mole.

2. The method of claim 1 wherein the Cu(I) salts are selected from the group consisting of Cu(I)Br, Cu(I)Cl, Cu(I)I, Cu(I) thiocyanate, and combinations thereof.

3. The method of claim 2 wherein the ligand is an aprotic bidendate.

4. The method of claim 3 wherein the aprotic bidendate is selected from the group consisting of 2,2' dipyridyl, diphosphates, $C_1$–$C_{20}$ alkyl substituted bipyridyl, and combinations thereof.

5. The method of claim 4 wherein the alkyl substituted bipyridyl is 4,4'-di-5-nonyl-2,2'-bipyridyl, 4,4'-di-tert-butylbipyridyl, 4,4'-diheptyl-2,2'-bipyridyl, or combinations thereof.

6. The method of claim 2 wherein reaction of step (a) is free radical polymerization of the copolymerizable monomers.

7. The method of claim 6 wherein the copolymerizable monomers of step (a) comprise an organic halide-containing vinyl monomer and a second monomer selected from the group consisting of acrylic acid produced by hydrolysis of trimethylsilyl acrylate, methacrylic acid produced by hydrolysis of trimethylsilyl methacrylate, vinyl pyrrolidone, acrylic acid esters of $C_1$–$C_{18}$ alcohols, methacrylic acid esters of $C_1$–$C_{18}$ alcohols, trimethylsilyl acrylate, trimethylsilyl methacrylate, styrene, alpha-methylstyrene, t-butylstyrene, vinyl acetate, vinyl propionate, 2-methoxyethyl acrylate, 2-ethoxyethyl acrylate, n-butyl methacrylate, isobutyl methacrylate, t-butyl acrylate, t-butyl methacrylate, 2-ethylhexyl methacrylate, methyl methacrylate, salts thereof, and mixtures thereof.

8. The method of claim 7 wherein the organic halide-containing vinyl monomer of step (a) is selected from the group consisting of (I)

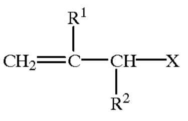

(II)

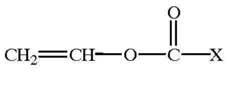

-continued (III)

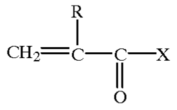

(IV)

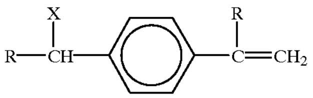

(V)

$CH_2{=}CH—O—R^4—X$ and combinations thereof, wherein R is methyl or hydrogen; X is a halogen atom; R, $R^1$ and $R^2$ are each independently methyl, hydrogen or methoxy; and $R^4$ is an alkyl group having from 1 to 8 carbon atoms.

9. The method of claim 8 wherein the polymeric backbone represents from about 50% to about 99% by weight of the graft polymer, and the plurality of polymeric side chains represent from about 1% to about 50% by weight of the graft polymer.

10. The method of claim 9 wherein the graft polymer is hydrophilic and has a polymeric backbone having a Tg value of less than about 35° C. and a plurality of polymeric side chains having a Tg value greater than about 50° C.

11. The method of claim 10 wherein the polymeric backbone has a Tg value of less than about 10° C. and the plurality of polymeric side chains have a Tg value of greater than 70° C.

12. The method of claim 9 wherein the graft polymer is hydrophilic and has a polymeric backbone having a Tg value greater than about 30° C. and a plurality of polymeric side chains having a Tg value less than about 10° C.

13. The method of claim 12 wherein the polymeric backbone has a Tg value greater than about 50° C. and the plurality of polymeric side chains have a Tg value less than about −20° C.

14. The method of claim 9 wherein the graft polymer is hydrophobic.

15. A method of making graft polymers, which process comprises the steps of:

(a) reacting by free radical polymerization copolymerizable monomers to form an organic polymeric backbone having a weight average molecular weight of from about 15,000 grams/mole to about 9,800,000 grams/mole and a plurality of organic halide moieties covalently bonded to the polymeric backbone and pendant from the polymeric backbone and then, without a separate purification or isolation step;

(b) reacting copolymerizable monomers with the organic halide moieties of the polymeric backbone by atom transfer free radical polymerization in the presence of a catalytic amount of a Cu(I) halide salt /2,2' bipyridyl complex to form a plurality of polymeric side chains covalently bonded to the polymeric backbone and pendant from the polymeric backbone, the polymeric side chains having an average molecular weight of from about 500 grams/mole to about 200,000 grams/mole, wherein the polymeric backbone and the plurality of polymeric side chains form graft polymers having a weight average molecular weight of from about 16,000 grams/mole to about 10,000,000 grams/mole.

16. The method of claim 15 wherein the Cu(I) halide salt is selected from the group consisting of Cu(I)Br, Cu(I)Cl, Cu(I)I, Cu(I) thiocyanate and combinations thereof.

17. The method of claim 16 wherein the copolymerizable monomers of step (a) comprise an organic halide-containing vinyl monomer and a second monomer selected from the group consisting of acrylic acid produced by hydrolysis of trimethylsilyl acrylate, methacrylic acid produced by hydrolysis of trimethylsilyl methacrylate, N,N-dimethyl acrylamide, dimethylaminoethyl methacrylate, quaternized dimethylaminoethyl methacrylate, vinyl pyrrolidone, acrylic acid esters of $C_1$–$C_{18}$ alcohols, methacrylic acid esters of $C_1$–$C_{18}$ alcohols, trimethylsilyl acrylate, trimethylsilyl methacrylate, styrene, alpha-methylstyrene, t-butylstyrene, vinyl acetate, vinyl propionate, 2-methoxyethyl acrylate, 2-ethoxyethyl acrylate, n-butyl methacrylate, isobutyl methacrylate, t-butyl acrylate, t-butyl methacrylate, 2-ethylhexyl methacrylate, methyl methacrylate, salts thereof, and mixtures thereof.

18. The method of claim 17 wherein the organic halide-containing vinyl monomer of step (a) is selected from the group consisting of (I)

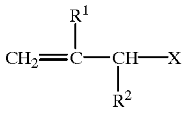

(II)

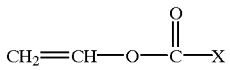

(III)

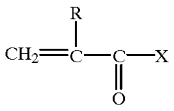

(IV)

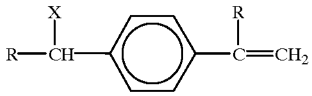

-continued (V)

$CH_2{=}CH{-}O{-}R^4{-}X$ and combinations thereof, wherein R is methyl or hydrogen; X is a halogen atom; R, $R^1$ and $R^2$ are each independently methyl, hydrogen or methoxy; and $R^4$ is an alkyl group having from 1 to 8 carbon atoms.

19. The method of claim 18 wherein the polymeric backbone represents from about 50% to about 99% by weight of the graft polymer, and the plurality of polymeric side chains represent from about 1% to about 50% by weight of the graft polymer.

20. The method of claim 19 wherein the graft polymer is hydrophilic and has a polymeric backbone having a Tg value of less than about 35° C. and a plurality of polymeric side chains having a Tg value greater than about 50° C.

21. The method of claim 20 wherein the polymeric backbone has a Tg value of less than about 10° C. and the plurality of polymeric side chains have a Tg value of greater than 70° C.

22. The method of claim 19 wherein the graft polymer is hydrophilic and has a polymeric backbone having a Tg value greater than about 30° C. and a plurality of polymeric side chains having a Tg value less than about 10° C.

23. The method of claim 22 wherein the polymeric backbone has a Tg value greater than about 50° C. and the plurality of polymeric side chains have a Tg value less than about −20° C.

24. The method of claim 7 wherein the copolymerizable monomers of step (a) further comprise a polysiloxane-containing vinyl macromonomer.

25. The method of claim 17 wherein the copolymerizable monomers of step (a) further comprise a polysiloxane-containing vinyl macromonomer.

26. The method of claim 19 wherein the graft polymer is hydrophobic.

* * * * *